(12) United States Patent
Sakthivel et al.

(10) Patent No.: US 7,365,194 B2
(45) Date of Patent: Apr. 29, 2008

(54) DIMER OF PHENAZINE-1-CARBOXYLIC ACID AND TO THE PROCESS OF PREPARATION THEREOF

(75) Inventors: Natarajan Sakthivel, Kalapet (IN); Radhakrishnan Sunish Kumar, Kalapet (IN)

(73) Assignee: Pondicherry University and Department of Biotechnology (IN)

( * ) Notice: Subject to any disclaimer, the term of this patent is extended or adjusted under 35 U.S.C. 154(b) by 404 days.

(21) Appl. No.: 10/888,786

(22) Filed: Jul. 9, 2004

(65) Prior Publication Data

US 2005/0227335 A1 Oct. 13, 2005

(30) Foreign Application Priority Data

Apr. 12, 2004 (IN) .................................. 696/2004

(51) Int. Cl.
*C07D 245/00* (2006.01)
*C07D 487/00* (2006.01)
*C07D 241/46* (2006.01)

(52) U.S. Cl. ...................................... 540/472; 544/347

(58) Field of Classification Search ...................... None
See application file for complete search history.

(56) References Cited

U.S. PATENT DOCUMENTS 5,658,794 A * 8/1997 Nair et al. ................ 435/253.3

OTHER PUBLICATIONS

Gurusiddaiah et al, "Characterization of an Antibiotic Produced by a Strain of Pseudomonas fluorescens Inhibitory to *Gaeumannomyces grammis* var. *tritici* and *Pythium* spp." Antimicrobial Agents and Chemotherapy, vol. 29(3), pp. 488-495 (1986).*

Brisbane et al, "Revised Structure for the Phenazine Antibiotic from Pseudomonas fluorescens 2-7.9 (NRRL B-15132)" Antimicrobial Agents and Chemotherapy, vol. 31(12), pp. 1967-1971 (1987).*

Mayer et al, "Effect of a short-term in vitro exposure to the marine toxin domoic acid on viability, tumor necrosis factor-alpha, matrix metalloproteinase-9 and superoxide anion release by rat neonatel microglia" BMC Pharmacology, vol. 1(7), pp. 1-13 (Published Oct. 2, 2001).*

* cited by examiner

*Primary Examiner*—Zachary C. Tucker
(74) *Attorney, Agent, or Firm*—The Webb Law Firm

(57) ABSTRACT

A dimer of phenazine-1-carboyxlic acid natural products from fluorescent pseudomonad bacterium and a method of preparing a dimer of phenazine-1-carboxylic acid natural product are disclosed herein. The method comprises growing the bacterium in a water based liquid medium under favorable pH and temperature with continuous agitation, extracting the dimer of phenazine-1-carboyxlic acid natural product from the medium by centrifugation using organic solvents, filtering the resultant emulsion to separate the aqueous layer in a separation funnel, isolating the crude dimer of phenazine-1-carboyxlic acid natural product from the organic layer by evaporating the organic solvent, and purifying the dimer of phenazine-1-carboxylic acid natural product by chromatography.

13 Claims, 12 Drawing Sheets

DIMER OF PHENAZINE-1-CARBOXYLIC ACID AND TO THE PROCESS OF PREPARATION THEREOF

FIELD OF INVENTION

This invention relates to dimer of phenazine-1-carboxylic acid natural product and to the process of preparation thereof.

BACKGROUND OF THE INVENTION

Fluorescent pseudomonads are commonly found in plant rhizosphere soil. Certain strains of these bacteria have been demonstrated to promote plant growth by suppressing plant pathogens. Mechanisms of these strains involve the production of siderophores, hydrogen cyanide (HCN) and antibiotics (Douglas and Gutterson, Applied and Environmental Microbiology 52:1183-1189 (1986)). Several disease-suppressive antibiotics, N-containing heterocyclics such as phenazine 1-carboxylic acid (PCA) (Gerber, Journal of Heterocyclic Chemistry 6:297-300 (1969); Thamashow et al. Applied and Environmental Microbiology 56:908-912 (1990); Slininger and Willbur, Applied and Environmental Microbiology 43:794-800 (1995)), phenazine-1-carboxamide (PCN) (Chin-A-Woeng et. al. Molecular Plant-Microbe Interaction 11:1069-1077 (1998)), acetamidophenol (Slininger et al. Applied Microbiology and Biotechnology 54:376-381 (2000)), pyrrol-type antibiotics (Hashimoto and Hattori, Bulletin of Chemical Society of Japan 39:410 (1966a) and Hashimoto and Hattori, Chemical and Pharmaceutical Bulletin 14:1314-1316 (1966b)), pyo-compounds (Hays et al. Journal of Biological Chemistry 159:725-750 (1945)), indoles (Wratten et al. Antimicrobial Agents and Chemotherapy 11:411-414 (1977)) and diacetylphloroglucinol (Shanahan et al. Applied and Environmental Microbiology 58:353-358 (1992) produced by fluorescent pseudomonads have been reported. The core biosynthetic pathway of phenazine is highly conserved in fluorescent *Pseudomonas* spp. ((Delaney et al. Journal of Bacteriology 183(1):318-327 (2001)). Species of fluorescent pseudomonads such as *P. fluorescens* (Thamashow et al. Applied and Environmental Microbiology 56:908-912 (1990)), *P. aureofaciens* (Toohey et al. Canadian Journal of Botany 43:1055-1062 (1965)) and *P. aeruginosa* (Fernandez and Pizaro, Journal of Chemotherapy A 771:99-104 (1997)) have been reported for the production of more than one phenazine. Although different phenazines have been found with the same structure, they differ in the derivatization of the heterocyclic core. These modifications of heterocyclic core largely determine the physical properties of phenazines and influence their antimicrobial activity against pathogens. However, the broad-spectrum activity of phenazines against fungi and bacteria is not understood so far. The biochemistry and genetics of phenazine synthesis has not been understood completely (Delaney et al. Journal of Bacteriology 183(1): 318-327 (2001)). Transgenic fluorescent *Pseudomonas* spp. that produce PCA as well as 2,4-diacetylphloroglucinol have been used as biocontrol agents against soil-borne fungal pathogens (*Pythium, Gaeumannomyces graminis* and *Rhizoctonia*) of food, fiber and oramental plants (Huang et al. U.S. Pat. No. 6,277,625 (2001). The PCA from *P. fluorescens* 2-79 has been characterized by Gurusiddaiah et al. (Antimicrobial Agents and Chemotherapy 29:488-495 (1986)) and the gene cluster involved in the biosynthesis has also been reported (McDonald et al. Journal of American Chemical Society 123: 9459-9460 (2001). Brisbane et al. (Antimicrobial Agents and Chemotherapy 31:1967-1971 (1987)) made criticism on the usefulness of PCA or PCA producing bacteria as effective biocontrol agents against phytopathogens in alkaline environments due to their pH dependency. In vitro tests clearly indicated that the PCA from *P. fluorescens* 2-79 is ineffective in alkaline pH due to complete ionization to an inactive carboxylate ion (Brisbane et al. Antimicrobial Agents and Chemotherapy 31: 1967-1971 (1987)).

OBJECTS OF THE INVENTION

An object of this invention is to propose a dimer of phenazine-1-carboxylic acid natural product.

Another object of this invention is to propose a process for producing a dimer of phenazine-1-carboxylic acid natural product.

Further object of this invention is to propose a dimer of phenazine-1-carboxylic acid natural product which shows antimicrobial activity at alkaline conditions.

Another further object of this invention is to propose a dimer of phenazine-1-carboxylic acid natural product as a potent cytotoxic agent.

Still further object of this invention is to propose a dimer of phenazine-1-carboxylic acid natural product as a potent antimicrobial agent.

BRIEF DESCRIPTION OF THE INVENTION

According to this invention there is provided a dimer of phenazine-1-carboxylic acid natural product by a fluorescent pseudomonad bacterium.

In accordance to this invention there is also provided a method of preparing dimer of phenazine-1-carboxylic acid natural product comprising growing the bacterium in a "water based liquid medium" under favorable pH and temperature with continuous agitation;

Extracting the dimer of phenazine-1-carboxylic acid natural product from the said water based liquid medium by step of centrifugation using organic solvents;

Filtering the resultant emulsion to separate the aqueous layer in a separation funnel;

Isolating the crude dimer of phenazine-1-carboxylic acid natural product from the organic layer by evaporating the organic solvent, and Purifying the dimer of phenazine-1-carboxylic acid natural product by chromatography.

BRIEF DESCRIPTION OF THE ACCOMPANYING FIGURES

DETAILED DESCRIPTION OF THE INVENTION

Figure 1:
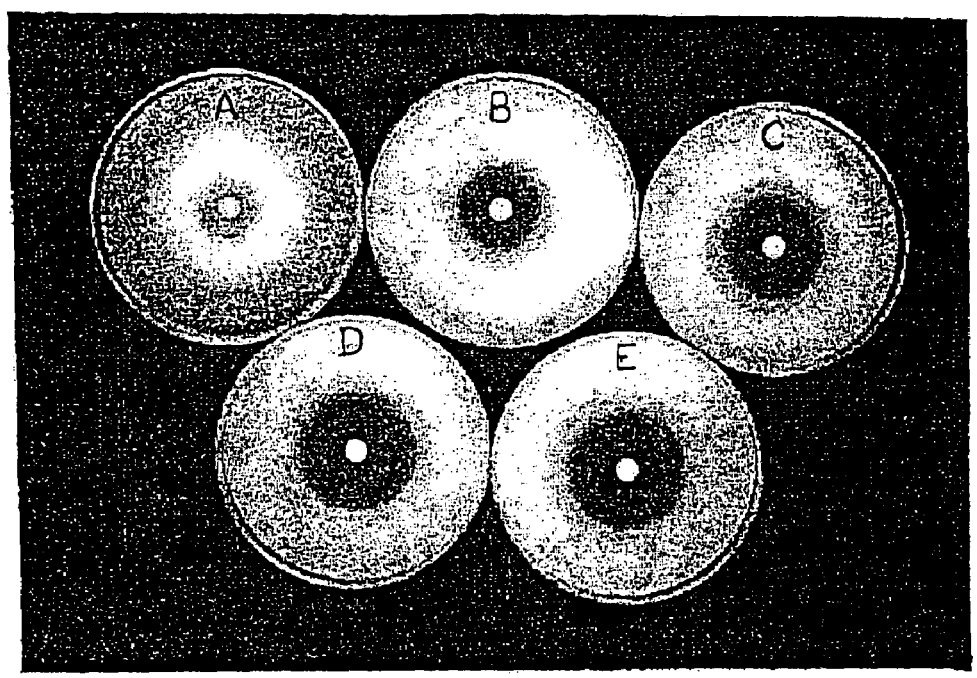
FIG. 1 shows the in vitro antifungal activity of the invention against *Macrophomina phaseolina* at different pH 5.5 (A), 6.5 (B), 7.5 (C), 8.5 (D) and 9.5 (E).

The process of present invention includes the production of dimer of phenazine-1-carboxylic acid natural product by a fluorescent pseudomonad bacterium.

The ingredient of "water-based semi-solid media" for initial growth of the bacterium is preferably about 2 to 30 g/L of protease peptone, most preferably about 20 g/L, with preferred amount of 1 ml/L to about 20 ml/L of glycerol with most preferably 15 ml/L. A preferred amount of mineral salts such as $K_2HPO_4$ of about 0.05 to about 3 g/L with most preferably 1.5 g/L and preferably 0.05 to about 3.0 g/L of $MgSO_4.7H_2O$ with most preferably 1.5 g/L. Solidifying substance, agar of preferably 10 to about 30 g/L with most preferably 15 g/L.

For the extraction of dimer of phenazine-1-carboxylic acid natural product, "water-based liquid media" was used. The "water-based liquid media" preferably contains any carbon source but most preferably glucose of 0.01 g/L to about 3 g/L with most preferably about 1 g/L and mineral salts such as, $Na_2HPO_4$ of preferably 0.005 to about 3.0 g/L, with most preferably 1.5 g/L, $NH_4Cl$ of preferably 0.001 to about 2 g/L, with most preferably 1 g/L, $MgSO_4.7H_2O$ of preferably 0.0001 to about 0.5 g/L, with most preferably about 0.02 g/L and ferric citrate of preferably about 0.0001 to about 0.5 g/L, with most preferably 1 g/L. For $^{15}N$ enrichment study preferably about 0.001 to about 2 g/L, with most preferably 1 g/L $^{15}N$ ammonium chloride was substituted in "water-based liquid media" instead of normal ammonium chloride. Water based semi-solid "potato infusion medium" containing potato-infusions of preferably about 100 to 800 g/L, with most preferably 300 g/L potatoes and any carbon source, most preferably glucose to an amount of preferably 0.5 to about 50 g/L, most preferably 20 g/L and solidifying substance, agar of preferably 10 to about 30 g/L with most preferably 15 g/L was used for the cultivation of fungi.

Isolation and Purification

For the production of dimer of phenazine-1-carboxylic acid natural product, fluorescent pseudomonad bacterium was grown in "water-based liquid media" under conditions of controlled and regulated pH and temperature with continuous agitation. Fluorescent pseudomonad bacterium grow and produce dimer of phenazine-1-carboxylic acid natural product preferably between temperatures of about 15° C. to about 37° C., more preferably at about 20° C. to about 30° C. and most preferably at about 25° C. Fluorescent pseudomonad bacterium grow and produce dimer of phenazine-1-carboxylic acid natural product at pH between 4 to about 9, more preferably about 5 to 7 and most preferably about 5.5 to 6.5. The culturing time is about 24 to about 200 hours, with more preferably about 48 to about 168 hours and most preferably about 72 to 120 hours. When cultivated under conditions as those described above, fluorescent pseudomonad bacterium can grow to cell densities up to about 10-25 g/L dry weight and produce dimer of phenazine-1-carboxylic acid natural product of about 150 µg/mL to about 200 µg/mL.

Controlling the oxygen in the "water-based liquid medium" is advantageous for the production of dimer of phenazine-1-carboxylic acid natural product. Preferably, oxygen levels are maintained at about 5% to about 50% saturation and more preferably at about 25% to 35% saturation. The concentration of oxygen in the medium can be maintained by sparging with air, pure oxygen or with gas mixtures including oxygen. Adjustment of agitation rate can also be used for adjusting the oxygen transfer rate. Dimer of phenazine-1-carboxylic acid natural product production from fluorescent pseudomonad bacterium can be enhanced by continuous culture methods with automatic feeding of glucose, to maintain the carbon source and an acid or base, such as sodium hydroxide or ammonium hydroxide to maintain the pH.

Dimer of phenazine-1-carboxylic acid natural product can be isolated and/or purified by any of a variety of methods known to those of skill in the art. Preferably the compound can be extracted by centrifugation or without centrifugation of the culture media. Most preferably, the cells grown in the "water-based liquid media" in the conditions mentioned herein are centrifuged at 5,000 g to about 10,000 g for 5 min to about 15 min to collect the supernatant. The compound is extracted by adding equal volume of organic solvents, preferably, benzene, hexane, ethyl acetate, acetone, acetonitrile, chloroform, dichloromethane, or any other suitable organic solvents or extraction buffers known, more preferably benzene, chloroform, dichloromethane or ethyl acetate to the culture media or the centrifuged supernatant by mixing thoroughly. The resultant emulsion was then filtered in cheesecloth and the aqueous layer was separated in a separation funnel. Alternatively, the resultant emulsion can also be purified by centrifugation or any other known purification process known to those of skill in art. The crude dimer of phenazine-1-carboxylic acid natural product was recovered from organic layer by evaporating the organic solvent.

The dimer of phenazine-1-carboxylic acid natural product is purified further by chromatography such as preparative TLC, HPLC or other methods known to those of skill in art.

Analyses of the Invention

Figure 3:
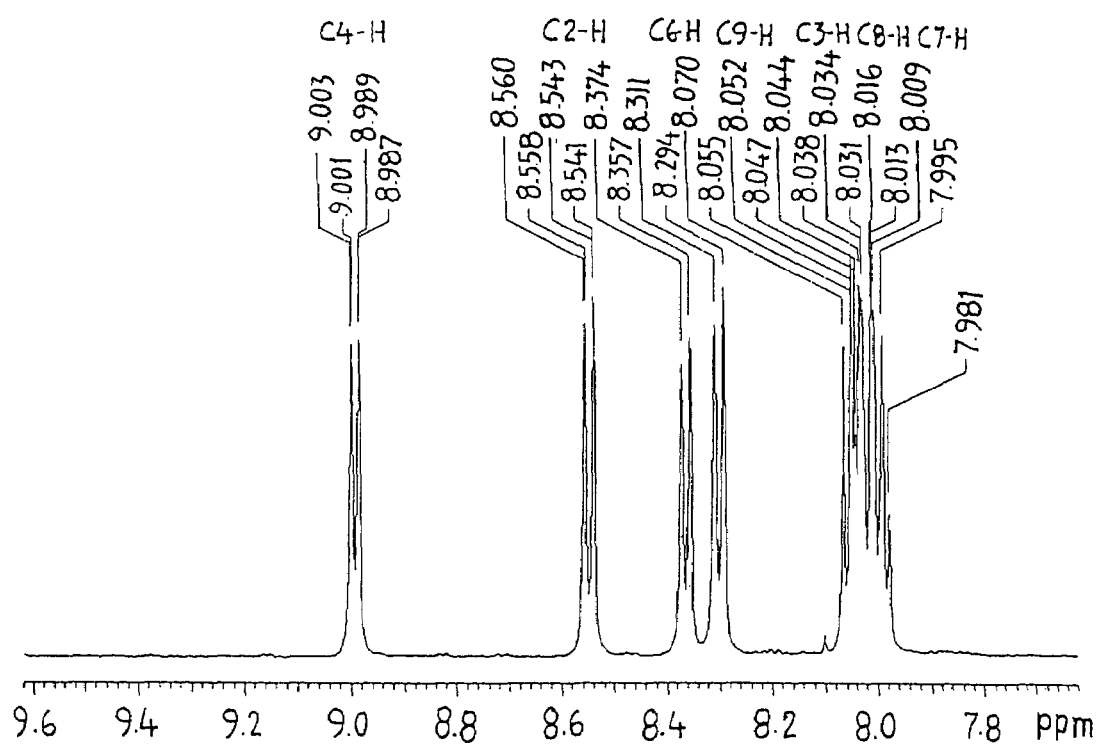
FIG. 3 shows the single-dimensional $^1$H Nuclear Magnetic Resonance (NMR) spectrum of the invention.
Figure 4:
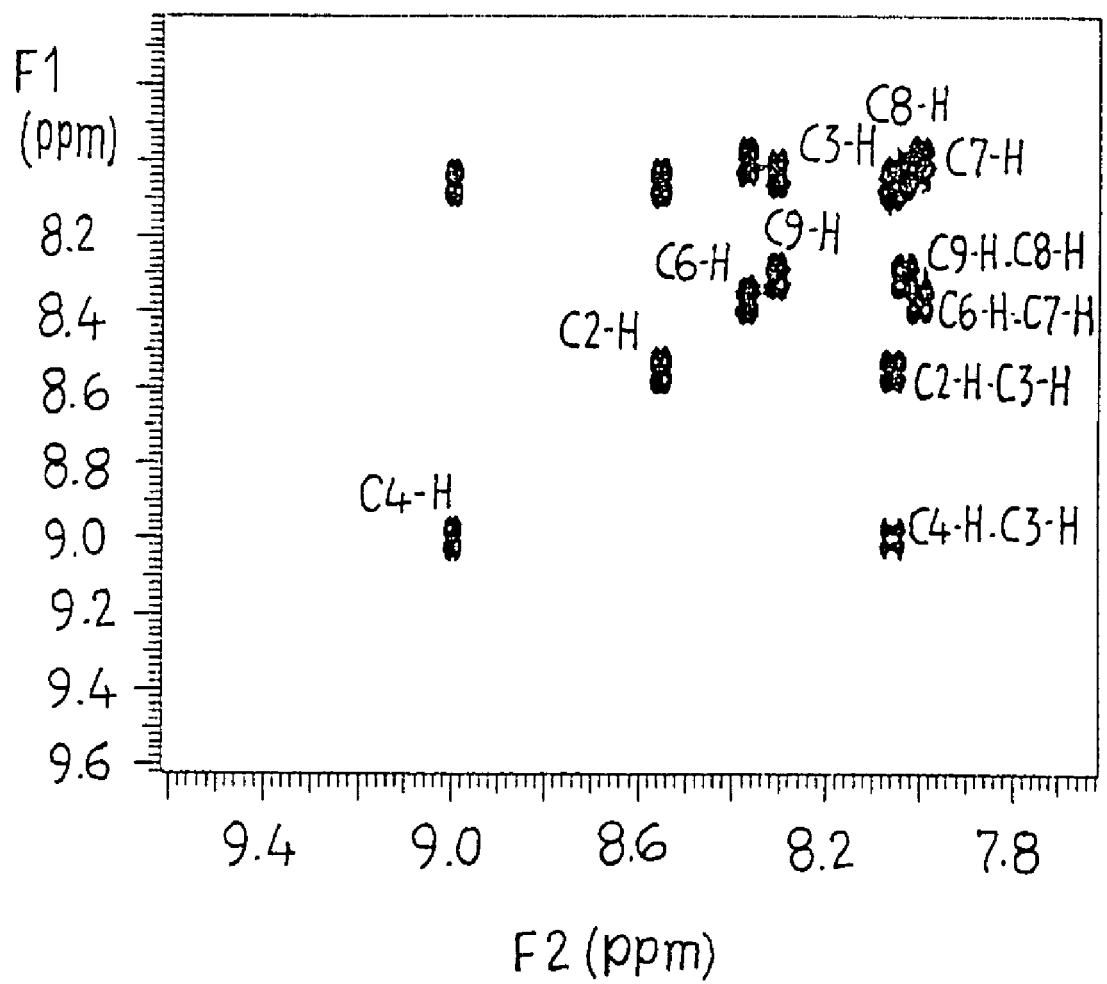
FIG. 4 shows the two-dimensional (DQF-COSY) NMR spectrum of the invention.
Figure 5:
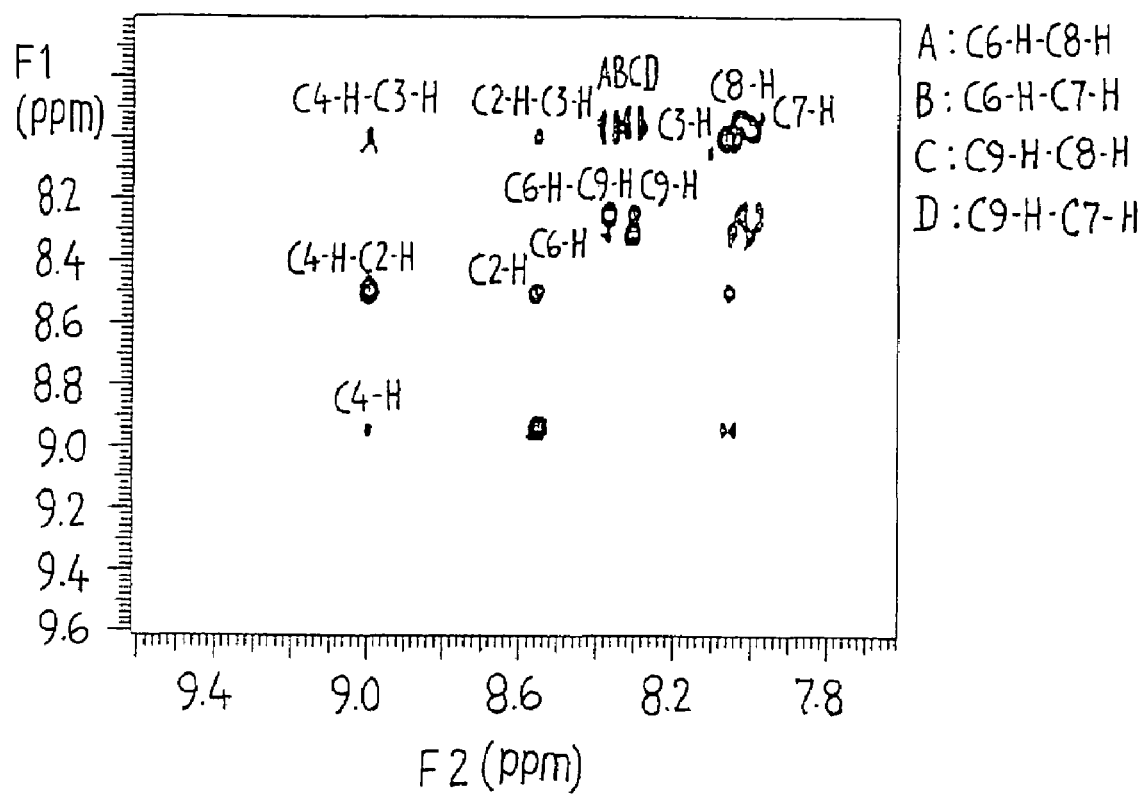
FIG. 5 shows the two-dimensional (TOCSY) NMR spectrum of the invention.
Figure 6:
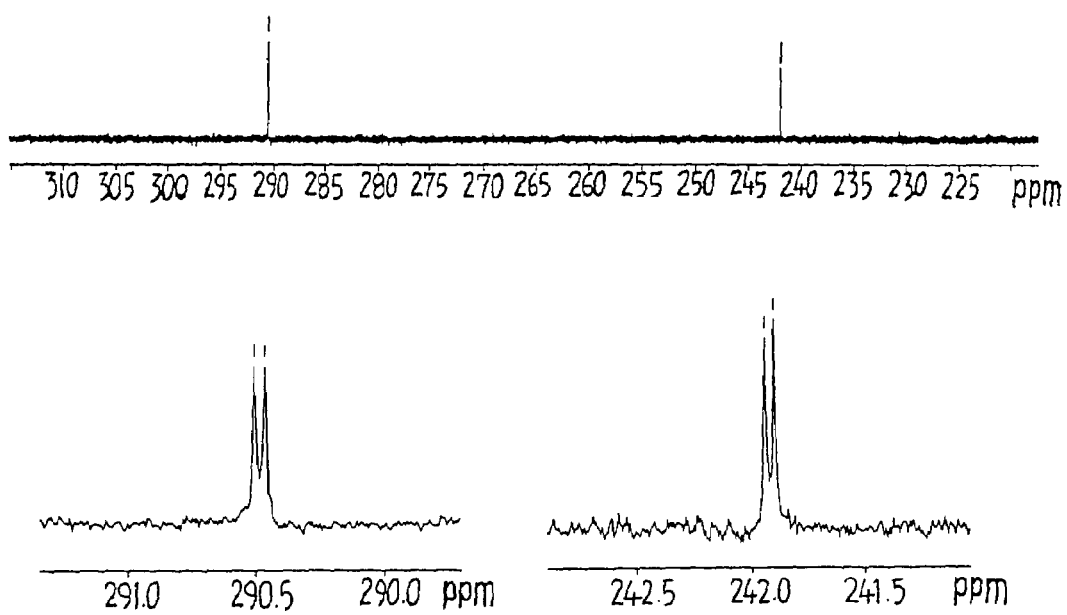
FIG. 6 shows the $^{15}$N NMR spectrum of the invention.

The FT-IR spectrum (FIG. 2) was obtained using ABB Bomen spectrometer. The single dimensional $^1H$ NMR (FIG. 3) and two-dimensional NMR (double quantum filtered correlated spectrometry (DQF-COSY) and total correlated spectrometry (TOCSY) spectra (FIGS. 4 and 5) were recorded in a 'state of art' 500 MHz Varian Unity-Plus spectrometer (Varian, Palo Alto Calif., USA), operating at 499.96 MHz for proton and 125.00 MHz for $^{13}C$ respectively, with a 5-mM triple resonance inverse detection probe. NMR data sets were acquired at 27° C. using $CDCl_3$ as solvent. $^{15}N$ NMR studies (FIG. 6) were done using Brucker DRX 500 NMR spectrometer. The proton signals were decoupled and $^{15}N$ signals were obtained. The spectrum of FAB-MS (FIG. 7) was recorded on a JOEL SX 102/DA-6000 Mass spectrometer using m-Nitrobenzyl alcohol as the matrix. Further, the spectra of ESI-MS (FIGS. 8 and 9) were recorded on a MICROMASS QUATTRO II triple quadrupole mass spectrometer using acetonitrile as the solvent.

Figure 2:
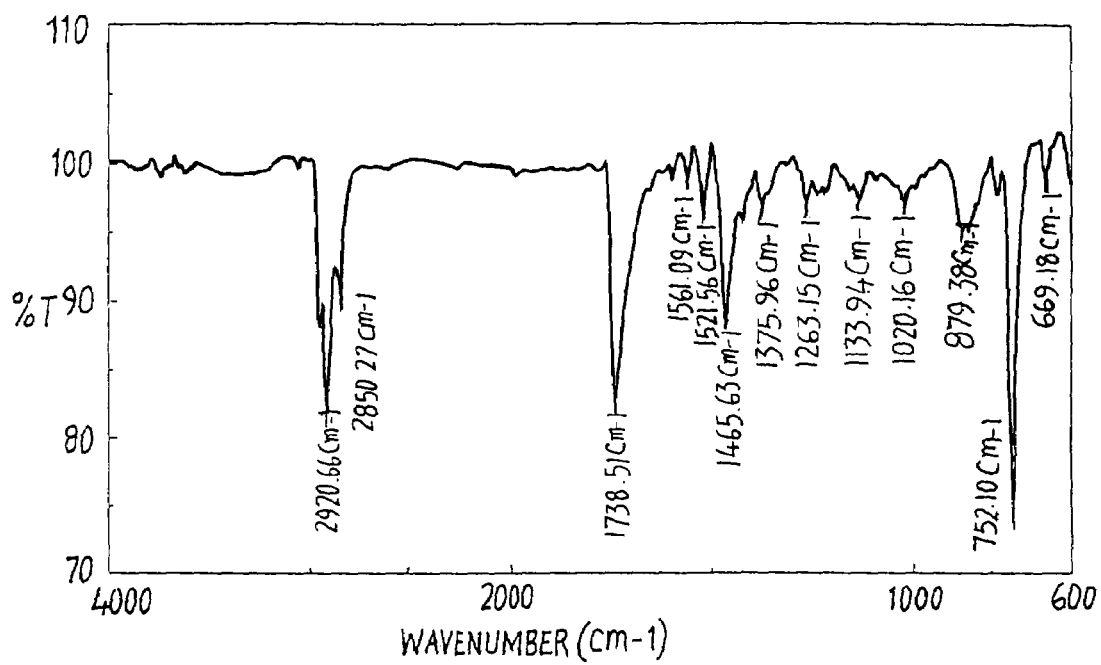
FIG. 2 shows the Fourier transform infrared (FT-IR) spectrum of the invention.

The FT-IR spectrum of the invention showed major absorption bands at 2920, 2850, 1738, 1561, 1521, 1465, and 1134 cm$^{-1}$. The N—N bond stretch of dimer of phenazine-1-carboxylic acid natural product was observed at 1134 cm$^{-1}$, (FIG. 2).

The aromatic region of the $^1$H NMR spectrum (FIG. 3) of the compound showed a typical resonance pattern of phenazine derivative as reported earlier (Gurusiddaiah et al. Antimicrobial Agents and Chemotherapy 29:488-495 (1986)). The signals resonated as doublet of a doublet at 8.98 (J=8.2 and 1.4 Hz) and 8.54 (J=8.0 and 1.4 Hz) ppm were assigned to protons at position 4 and 2 respectively. In the 2D $^1$H-$^1$H DQF-COSY NMR spectrum (FIG. 4) both of these signal showed a common cross peak at 8.05 ppm due to proton at position 3. This assignment was further confirmed through $^1$H-$^1$H 2D-TOCSY spectrum (FIG. 5) showing cross peaks at 8.05 and 8.54 ppm to the down field resonance (8.98 ppm) due to proton at position 4. The 2D $^1$H-$^1$H DQF-COSY (FIG. 4) and TOCSY (FIG. 5) spectra showed the resonance at 8.30 assigned to proton at position 9 showed a common cross peak with proton at position 8 resonated at 8.05 ppm. Similarly proton at position 6 assigned to peak at 8.36 ppm showed a common cross peak at 7.99 ppm due to proton at 7. The most low field signal resonated at 15.6 ppm was unambiguously assigned to carboxylic proton. The complete $^1$H NMR chemical shift assignment (ppm) and coupling constants [J(H, H)/(Hz)] with two-dimensional (DQF-COSY) of dimer of phenazine-1-carboxylic acid natural product are shown in Table 1.

The $^{15}$N NMR spectrum also confirmed the dimer of phenazine-1-carboxylic acid natural product. The doublets at ppm 290.5 and 241.9 (FIG. 6) in $^{15}$N NMR further confirmed the N—N bond between the monomer molecule to form dimer of phenazine-1-carboxylic acid natural product.

Figure 7:
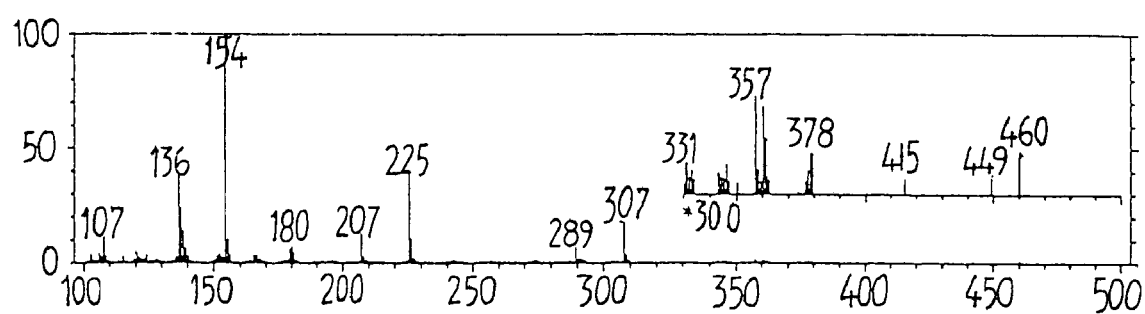
FIG. 7 shows the Fast atom bombardment mass spectrum (FAB-MS) of the invention.
Figure 8:
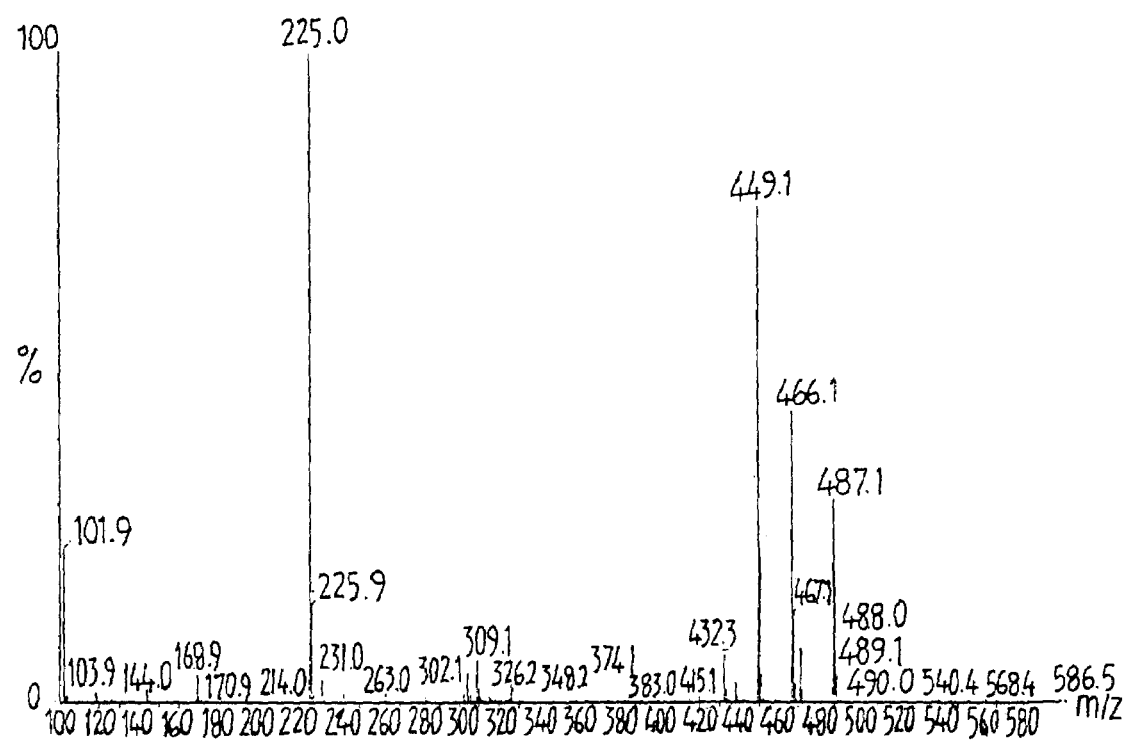
FIG. 8 shows the electro-spray mass spectrum (ESI-MS+ve) of the invention.
Figure 9:
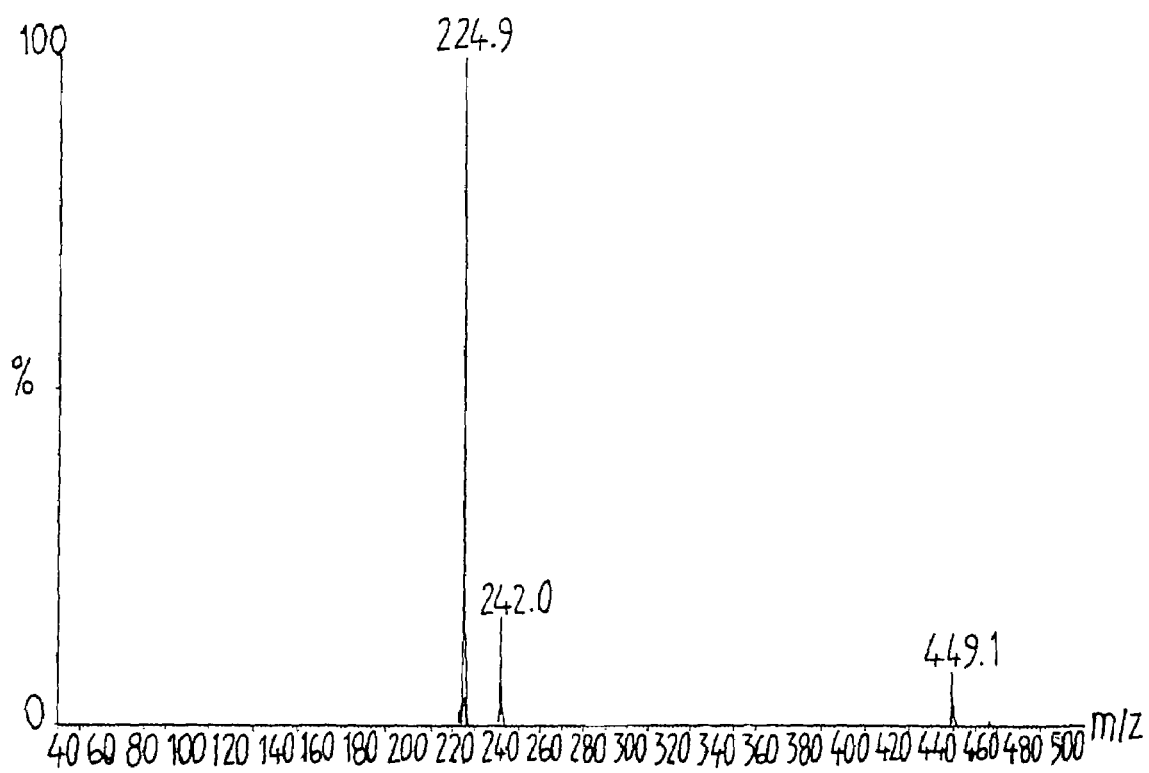
FIG. 9 shows the daughters of m/z 466 of ESI-MS+ve of the invention.
Figure 10:
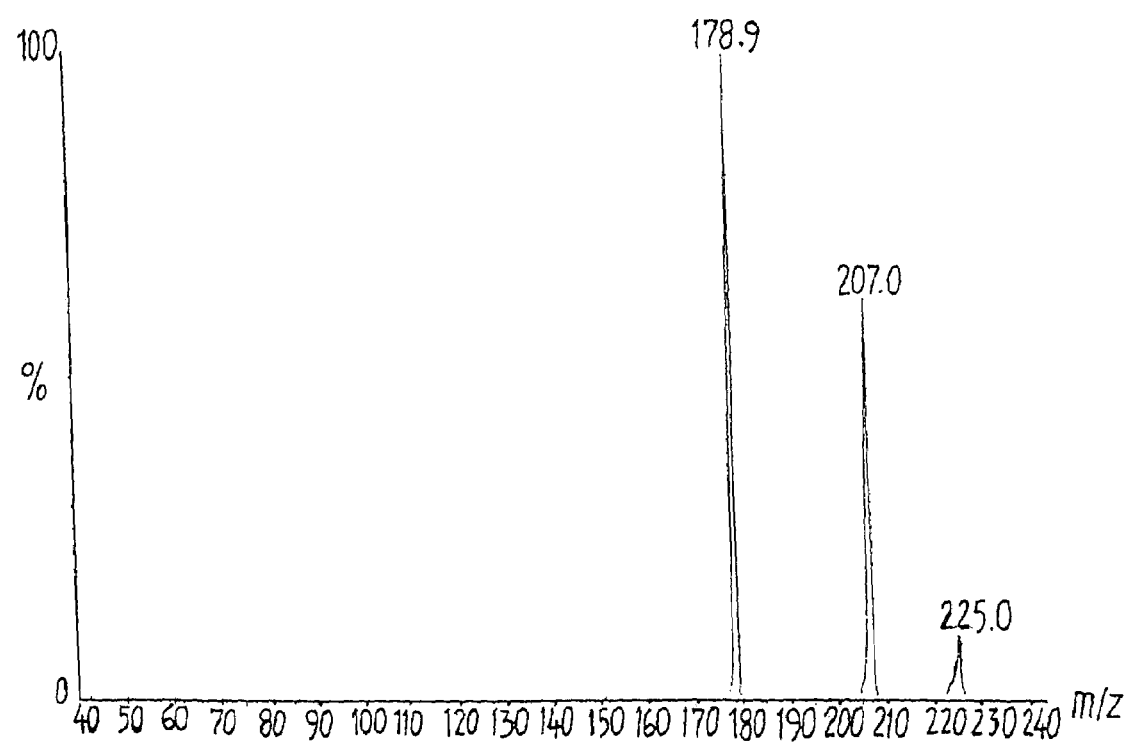
FIG. 10 shows the daughters of m/z 225 of ESI-MS+ve of the invention.
Figure 11:
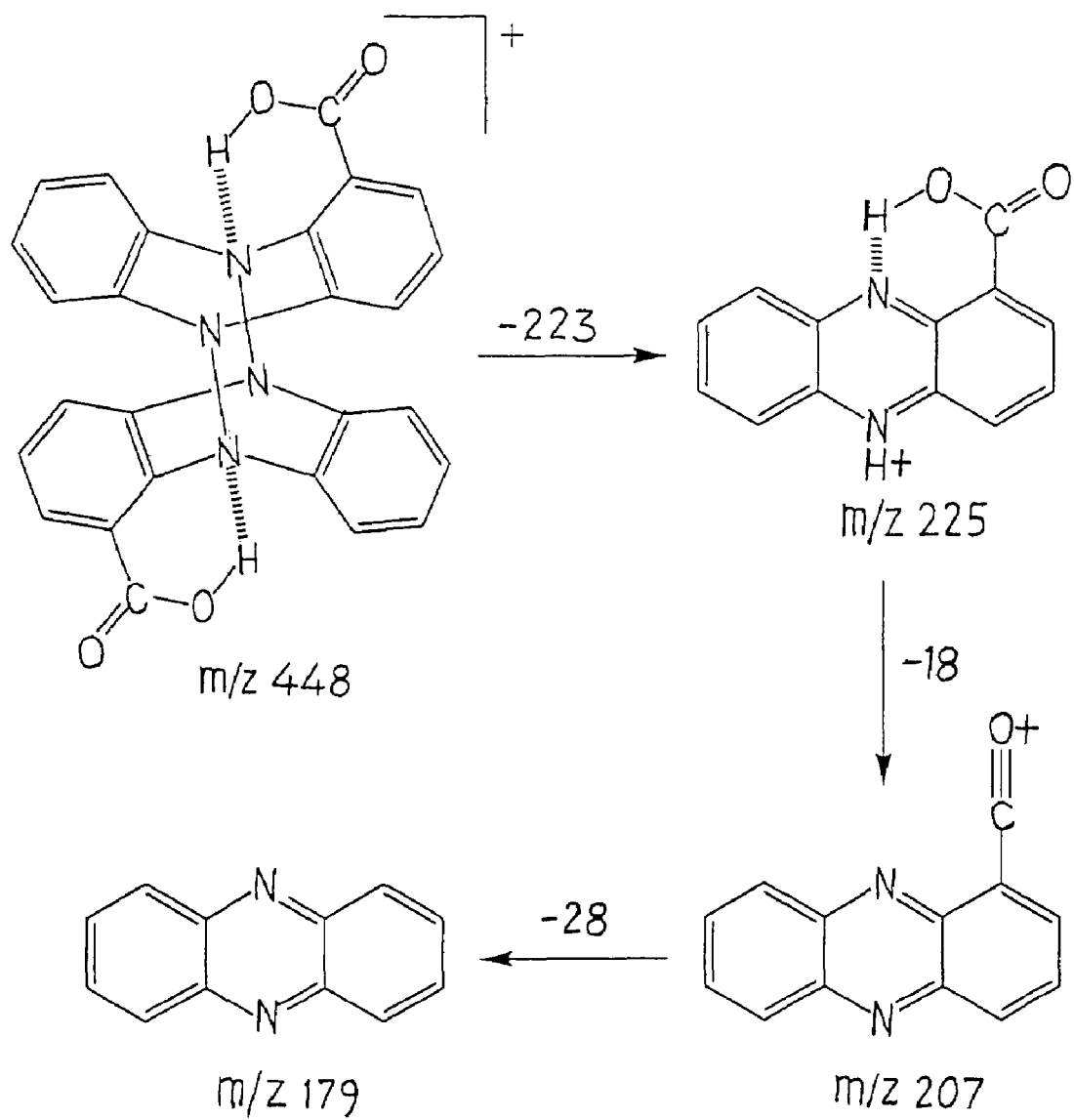
FIG. 11 shows the fragmentation pattern of dimer of phenazine-1-carboxylic acid natural product based on daughters of ESI-MS+ve data.
Figure 12:
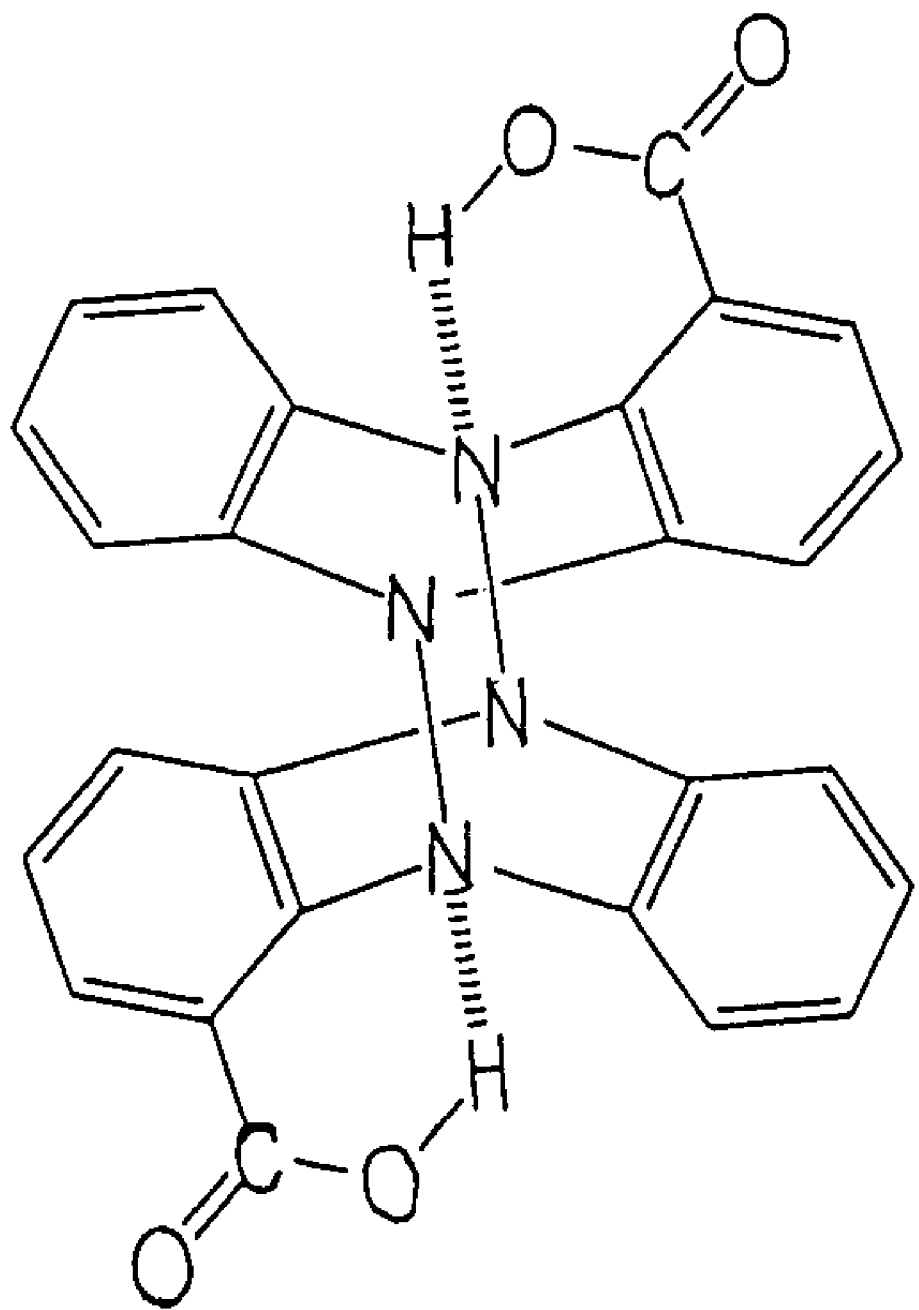
FIG. 12 shows proposed structure of dimer of phenazine-1-carboxylic acid natural product.

The FAB mass spectrum (FIG. 7) of dimer of phenazine-1-carboxylic acid natural product gave an M+H peak at m/z 449 indicating that the molecular mass of the antibiotic is 448. The fragmentation peaks were observed at m/z 415, 360, 225, 207, 180 and 154 (FIG. 7). The base peak was observed at m/z 154. The electro-spray MS also gave an M+H peak at m/z 449 with M+NH4 peak at m/z 466 and M+K peak at m/z 487 (FIG. 8). The daughters of 466 ES+ were seen at m/z 449, 242 and 225 (M+H, 100%) as shown in FIG. 9 and the daughters of 225 ES+ were observed in FIG. 10 at m/z 207 and 179 (100%).

Cytotoxicity of Dimer of Phenazine-1-Carboxylic Acid Natural Product

Dimer of phenazine-1-carboxylic acid natural product was tested for cytotoxycity using 3-(4,5-dimethylthiazol-2-yl)-2,5-diphenyltetrazolium bromide (MTT) assay. The cells (3×10$^3$/well) were cultured in 96-well plates with different concentrations of dimer of phenazine-1-carboxylic acid natural product (1-50 μg) for 24 hr at 37° C. At the end of incubation, 20 μL MTT (5 mg/mL) was added and cells were incubated at 37° C. After 4 hr, MTT was removed and 100 μL of DMSO was added. Cell viability was determined by measuring the absorbance at a test wavelength of 570 nm.

Antimicrobial Activity of Dimer of Phenazine-1-Carboxylic Acid Natural Product

Dimer of phenazine-1-carboxylic acid natural product was tested for antimicrobial activity in acidic and neutral pH against microorganisms following agar diffusion method, using the purified antibiotic. Sterile paper discs (6 mm) were separately treated with different concentration of dimer of phenazine-1-carboxylic acid natural product (2-14 μg/mL) and placed on the surface of PDA agar plates that were spread-inoculated with test organisms. Assay plates were incubated at 28° C. for 3 days to observe the zone of growth-inhibition of test microorganisms.

Present invention thus describes the isolation, purification and characterization of the novel, dimer of phenazine-1-carboxylic acid natural product from a broad-spectrum antagonistic fluorescent pseudomonad bacterium. The experimental data provided in this invention now firmly establish existence of the dimer of phenazine-1-carboxylic acid natural product and its cytotoxicity as well as novel antimicrobial activity in acidic and alkaline pH. The drawbacks on applications of other phenazines in alkaline environment due to complete ionization have been overcome by the present invention.

EXAMPLE 1

Production of dimer of phenazine-1-carboxylic acid natural product Fermentation methods were developed for the production of dimer of phenazine-1-carboxylic acid natural product.

Materials and Methods

Preparation of Inoculum

An aliquot of cells stored as lyophilized samples was used to prepare the pre-inoculum of 500 mL in "water based liquid medium" composed of (g/l) peptone (20), glycerol (10), $K_2HPO_4$ (1.5) and Mg $So_4.7H_2O$ (1.5). Approximately a loop full of cells was used to inoculate 500 mL portion of medium in 1 liter flask. Flask was incubated with shaking for 24 hours at 27° C. The content of the flask was used to inoculate fermentation broth.

Fermentation Stage

Fermentation broth was composed of (g/L) glucose (1), $Na_2HPO_4$ (4), $K_2HPO_4$ (1.5), $NH_4Cl$ (1), $MgSO_4.7H_2O$ (0.02) and ferric citrate (0.005) in distilled water. The pH was adjusted to 7.0 before sterilization. Fermentation was carried out at 25° C. for 120 hr.

Results and Conclusion

Several fermentation methods have been shown to produce dimer of phenazine-1-carboxylic acid natural product from fluorescent pseudomonad bacterium.

EXAMPLE 2

Isolation and Purification of Dimer of Phenazine-1-Carboxylic Acid Natural Product Methods were developed for isolation and purification of dimer of phenazine-1-carboxylic acid natural product from fluorescent pseudomonad bacterium.

Material and Methods

The whole fermentation broth after harvest was centrifuged at 5,000 g for 5 min to collect the supernatant (fraction A). To fraction A equal volume of ethyl acetate was added and mixed in a rotary shaker for 3 hr. The resultant emulsion was then filtered through cheesecloth and the aqueous layer (fraction B) and organic layer (fraction C) was separated in a separating funnel. Fraction C was evaporated in vacuo to yield the crude fraction D. Fraction D was adsorbed on a silica gel, applied to a previously packed silica column and eluted with chloroform. The active fractions were collected, applied on to the pre-coated preparative thin layer chromatography (TLC) plates (G60, 20 cm×20 cm, Selecto Scientific, GA) and developed with solvent system of isopropanol-ammonia-water (8:1:1). The plates were examined under UV at 254 and 365 nm. The active greenish yellow spot was scraped and extracted from silica gel using chloroform. The purity of the antibiotic was confirmed by high-performance liquid chromatography (HPLC). A single peak was detected in a Phenomenex Luna (2) C18 reverse phased column (250 mm×4.6 mm) when acetonitrile and water (both containing 0.1% trifluoroacetic acid) in a 30 to 70% linear gradient was used as the solvent system with a flow rate of 0.7 ml min$^{-1}$. The chromatogram was detected at 254 nm. This process yielded around 60 mg of purified dimer of phenazine-1-carboxylic acid natural product per liter of fermentation media.

Results and Conclusion

Regular purification methods normally used to purify antibiotics from pseudomonad strains resulted in the purification of dimer of phenazine-1-carboxylic acid natural product from fermentation broth.

EXAMPLE 3

Determination of Structure of Dimer of Phenazine-1-Carboxylic Acid Natural Product FT-IR, NMR and Mass spectrometry determined the structure of dimer of phenazine-1-carboxylic acid natural product.

Methods and Results

The FT-IR spectrum of the invention showed major absorption bands at 2920, 2850, 1738, 1561, 1521, 1465 and 1134 cm$^{-1}$. The N—N bond stretch of dimmer phenazine-1-carboxylic acid natural product was observed at 1134 cm$^{-1}$ (FIG. 2).

$^1$H NMR spectrum signals resonated as doublet of a doublet at 8.98 (J=8.2 and 1.4 Hz) and 8.54 (J=8.0 and 1.4 Hz) ppm was assigned to protons at position 4 and 2 respectively. In the 2D $^1$H-$^1$H DQF-COSY NMR spectrum (FIG. 4) both of these signal showed a common cross peak at 8.05 ppm due to proton at position 3. This assignment was further confirmed through $^1$H-$^1$H 2D-TOCSY spectrum (FIG. 5) showing cross peaks at 8.05 and 8.54 ppm to the down field resonance (8.98 ppm) due to proton at position 4. The 2D $^1$H-$^1$H DQF-COSY (FIG. 4) and TOCSY (FIG. 5) spectra showed the resonance at 8.30 assigned to proton at position 9 showed a common cross peak with proton at position 8 resonated at 8.05 ppm. Similarly proton at position 6 assigned to peak at 8.36 ppm showed a common cross peak at 7.99 ppm due to proton at 7. The most low field signal resonated at 15.6 ppm was unambiguously assigned to carboxylic proton. The complete assignments based on these two-dimensional NMR experiments are shown in Table 1.

The $^{15}$N NMR spectrum also confirmed the dimer of phenazine-1-carboxylic acid natural product. The doublets at ppm 290.5 and 241.9 (FIG. 6) in $^{15}$N NMR further confirmed the N—N bond between the monomer molecules to form dimer of phenazine-1-carboxylic acid natural product.

The FAB mass spectrum (FIG. 7) of the dimer of phenazine-1-carboxylic acid natural product gave an M+H peak at m/z 449 indicating that the molecular mass of the antibiotic is 448. The fragmentation peaks were observed at m/z 415,360,225,207, 180 and 154 (FIG. 7). The base peak was observed at m/z 154. The electro-spray MS also gave an M+H peak at m/z 449 with M+NH4 peak at m/z 466 and M+K peak at m/z 487 (FIG. 8). The daughters of 466 ES+ were seen at m/z 449,242 and 225 (M+H, 100%) as shown in FIG. 9 and the daughters of 225 ES+ were observed in FIG. 10 at m/z 207 and 179 (100%).

EXAMPLE 4

Determination of Cytotoxycity of Dimer of Phenazine-1-Carboxylic Acid Natural Product Cytotoxycity of dimer of phenazine-1-carboxylic acid natural product against cell lines was determined by MTT assay. For MTT assay, the cells (3×10$^3$/well) were cultured in 96-well plates with different concentrations of dimer of phenazine-1-carboxylic acid natural product for 24 hr at 37° C. At the end of incubation, 20 µL MTT (5 mg/mL) was added and cells were incubated at 37° C. After 4 hr, MTT was removed and 100 µL of DMSO was added. Cell viability was determined by measuring the absorbance at a test wavelength of 570 nm. The results are presented in Table 2.

EXAMPLE 5

Determination of Antimicrobial Activity of Dimer of Phenazine-1-Carboxylic Acid Natural Product in Acidic and Alkaline pH Antimicrobial activity was determined in vitro by obtaining the minimum inhibitory concentration (MIC) of dimer of phenazine-1-carboxylic acid natural product using a standard agar dilution test or a disc-diffusion test. Dimer of phenazine-1-carboxylic acid natural product showed antimicrobial activity in acidic and alkaline pH against plant, animal and human pathogens.

Test compound was dissolved in chloroform at various concentrations, separately loaded on to sterile filter paper discs (Whatman No.1, 6 mm diameter) and placed on the surface of agar plates pre-inoculated with the test pathogens. Assay plates were incubated at 27° C. for 72 hr for fungi and 27° C. to about 37° C. for 48 hr for bacteria. The results are presented in Table 3.

TABLE 1

Complete $^1$H NMR chemical shift assignments (ppm) and coupling constants [J (H, H)/Hz] with two-dimensional data (DQF-COSY) of dimer of phenazine-1-carboxylic acid natural product

| Proton | Chemical shift (ppm) | Coupling constant J(H, H)/(Hz) | DQF-COSY $^1$H Cross-peaks (ppm) |
|---|---|---|---|
| H-2 | 8.54 | J(2, 3) = 8.0, J(2, 4) = 1.4 | 8.05 |
| H-3 | 8.05 | J(3, 2) = 8.0, J(3, 4) = 8.2 | 8.53, 8.98 |
| H-4 | 8.98 | J(4, 3) = 8.2, J(4, 2) = 1.4 | 8.05 |
| H-6 | 8.36 | J(6, 7) = 7.8, J(6, 8) = 1.2 | 8.00 |
| H-7 | 7.99 | m | 8.37, 8.05 |
| H-8 | 8.05 | m | 8.00, 8.31 |
| H-9 | 8.30 | J(9, 8) = 8.1, J(9, 7) = 1.0 Hz | 8.05 |
| COOH | 15.6 | s | — |

TABLE 2

Cytotoxicity of dimer of phenazine-1-carboxylic acid natural product

| Concentration | OD @ 570 nm* | Cell viability (%) |
|---|---|---|
| 0 | 1.233 | |
| 1 | 0.531 | 45.03 |
| 10 | 0.472 | 40.03 |
| 25 | 0.366 | 31.07 |
| 50 | 0.285 | 24.17 |

*Average of three replicates

TABLE 3

Antimicrobial activity of dimer of phenazine-1-carboxylic acid natural product

| Organism | MIC (µg/mL) |
| --- | --- |
| Colletotrichum gleosporoides | 7 |
| C. capsici | 7 |
| C. falcatum | 5 |
| Sarocladium oryzae | 3 |
| Macrophomina phaeseolina | 12 |
| Rhizoctonia solani | 2 |
| Fusarium oxysporum sub sp. cubense | 7 |
| Botrytis cinera | 14 |
| Staphylococcus aureus | >120 |
| Pseudomonas aeruginosa | >90 |
| Escherichia coli | >100 |
| Salmonella typhimurium | >120 |

We claim:

1. An isolated and/or purified dimer of phenazine-1-carboxylic acid natural produced by a fluorescent *Pseudomonad* bacterium.

2. A method of preparing a dimer of a phenazine-1-carboxylic acid natural product by bacterial fermentation comprising growing a fluorescent *Pseudomonad* bacterium which produces the dimer of phenazine-1carboxylic acid in water based liquid medium under favorable pH and temperature with continuous agitation;

Extracting the dimer of phenazine-1-carboxylic acid natural product from the said water based liquid medium by step of centrifugation using organic solvents;

Filtering the resultant emulsion to separate the aqueous layer in a separation funnel;

Isolating the crude dimer of phenazine-1-carboxylic acid natural product from the organic layer by evaporating the organic solvent, and Purifying the dimer of phenazine-1-carboxylic acid natural product by chromatography.

3. The method as claimed in claim 2, wherein the water based liquid medium comprises of 0.01 g/L to 3 g/L of carbon source, 0.5 to 6 g/L of mineral salt and 10 to 3 g/L agar.

4. The method as claimed in claim 2, wherein the bacterium is grown at a temperature range of 15 to 37° C.

5. The method as claimed in claim 2, wherein the bacterium is grown at a pH range of 4 to 9.

6. The method as claimed in claim 2, wherein the culturing time is about 24 to 200 hours.

7. The method as claimed in claim 2, wherein the organic solvents are selected from benzene, hexane, ethyl acetate, acetone, acetonitrile, chloroform, and dichloromethane.

8. The method as claimed in claim 7, wherein said organic solvents are selected from benzene, chloroform, dichloromethane and ethyl acetate.

9. The method as claimed in claim 2, wherein the step of purification is preparative TLC or HPLC.

10. The method as claimed in claim 3, wherein the carbon source is glucose.

11. The method as claimed in claim 2, wherein the bacterium is grown at a temperature range of 20 to 30° C.

12. The method as claimed in claim 2, wherein the bacterium is grown at a pH range of 5 to 7.

13. The method as claimed in claim 2, wherein the culturing time is about 48 to 168 hours.

* * * * *

UNITED STATES PATENT AND TRADEMARK OFFICE
CERTIFICATE OF CORRECTION

PATENT NO. : 7,365,194 B2  Page 1 of 1
APPLICATION NO. : 10/888786
DATED : April 29, 2008
INVENTOR(S) : Sakthivel et al.

It is certified that error appears in the above-identified patent and that said Letters Patent is hereby corrected as shown below:

Column 9, line 21, Claim 1, "acid natural produced" should read
-- acid natural product produced --

Column 10, line 7, Claim 3, "comprises of" should read
-- comprised of --

Signed and Sealed this

Twenty-sixth Day of August, 2008

JON W. DUDAS
*Director of the United States Patent and Trademark Office*